(12) United States Patent
Blume et al.

(10) Patent No.: US 8,135,185 B2
(45) Date of Patent: Mar. 13, 2012

(54) LOCATION AND DISPLAY OF OCCLUDED PORTIONS OF VESSELS ON 3-D ANGIOGRAPHIC IMAGES

(75) Inventors: Walter M. Blume, St. Louis, MO (US); Jeffrey M. Garibaldi, St. Louis, MO (US); Heather Drury, St. Louis, MO (US); Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1153 days.

(21) Appl. No.: 11/874,895

(22) Filed: Oct. 18, 2007

(65) Prior Publication Data

US 2008/0097200 A1 Apr. 24, 2008

Related U.S. Application Data

(60) Provisional application No. 60/862,418, filed on Oct. 20, 2006.

(51) Int. Cl.
*G06K 9/00* (2006.01)

(52) U.S. Cl. ........ 382/128; 128/920; 128/921; 128/922; 128/923; 128/924; 600/407; 600/408; 600/409; 600/410; 600/411

(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | | |
|---|---|---|---|
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |

(Continued)

FOREIGN PATENT DOCUMENTS

WO WO2005/031635 4/2005

OTHER PUBLICATIONS

International Search Report and Written Opinion for corresponding PCT/US07/081942 Dated: Mar. 24, 2008 pp. 10.

*Primary Examiner* — Atiba O Fitzpatrick
(74) *Attorney, Agent, or Firm* — Harness, Dickey & Pierce, P.L.C.

(57) ABSTRACT

A method of finding the location of an occluded portion of a blood vessel relative to a three-dimensional angiographic image of a subject's vasculature includes identifying the location of the occluded portion of the blood vessel on each of a series of displayed two dimensional images derived from the three dimensional image data in planes substantially transverse to direction of the occluded portion of the vessel. The identified locations in the occluded portion of the vessel can then be used to determine the path of the occluded portion of the vessel.

25 Claims, 4 Drawing Sheets

U.S. PATENT DOCUMENTS

| | | |
|---|---|---|
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,842,638 B1* | 1/2005 | Suri et al. .................. 600/425 |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 2001/0036303 A1 | 11/2001 | Maurincomme et al. |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0118869 A1* | 8/2002 | Knoplioch et al. .......... 382/131 |
| 2002/0177789 A1 | 11/2002 | Ferry et al. |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0223636 A1 | 11/2004 | Edic et al. |
| 2004/0249262 A1 | 12/2004 | Werp et al. |
| 2004/0249263 A1 | 12/2004 | Creighton, IV |
| 2004/0249270 A1* | 12/2004 | Kondo et al. ................. 600/425 |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0098010 A1 | 5/2006 | Dwyer et al. |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2008/0004595 A1 | 1/2008 | Viswanathan |
| 2008/0006280 A1 | 1/2008 | Aliberto et al. |
| 2008/0015427 A1 | 1/2008 | Kastelein et al. ............ 600/410 |
| 2008/0015670 A1 | 1/2008 | Pappone ...................... 607/122 |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |

* cited by examiner

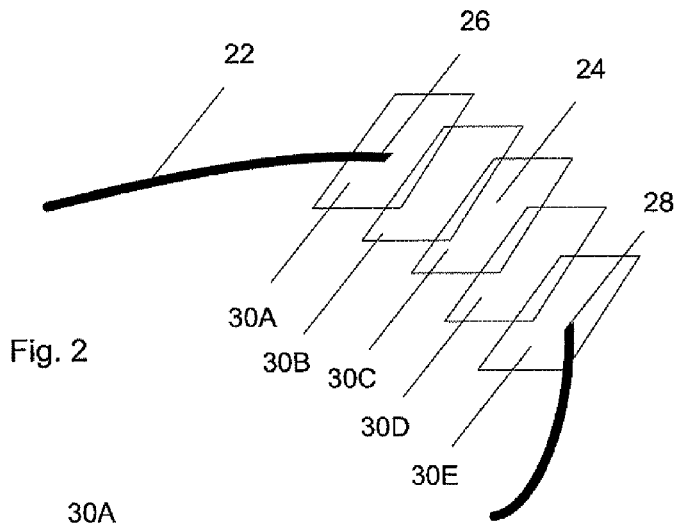
Fig. 2
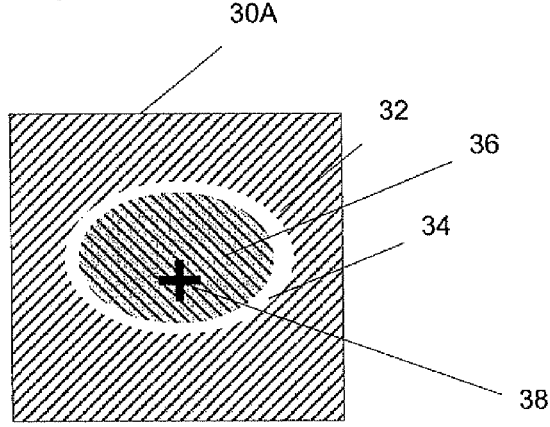
Fig. 3
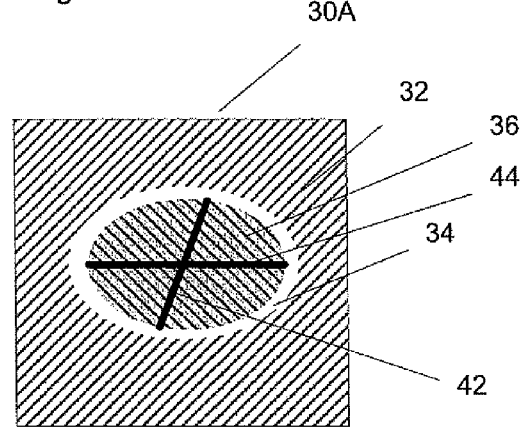
Fig. 5
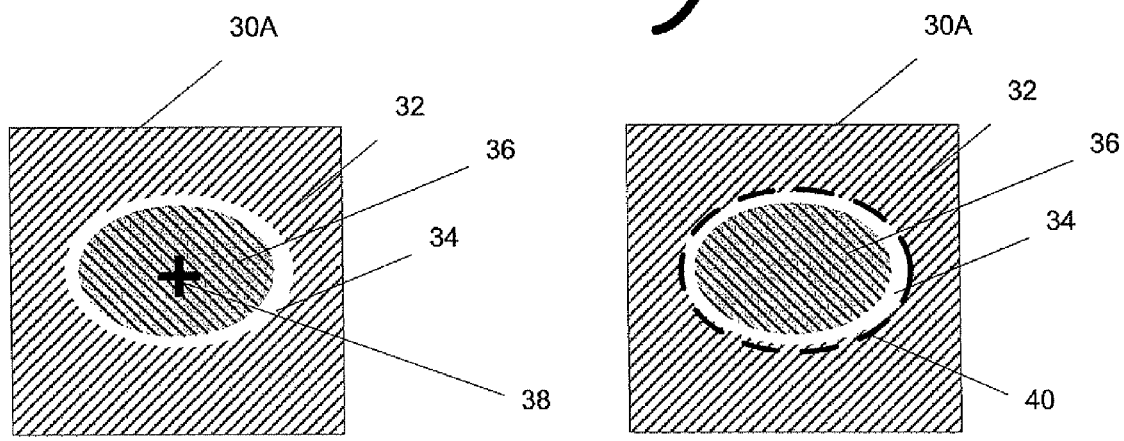
Fig. 4
Fig. 6

LOCATION AND DISPLAY OF OCCLUDED PORTIONS OF VESSELS ON 3-D ANGIOGRAPHIC IMAGES

CROSS-REFERENCE TO RELATED APPLICATION

This application claims priority to prior U.S. Provisional Patent Application Ser. No. 60/862,418, filed Oct. 20, 2006, the entire disclosure of which is incorporated herein by reference.

BACKGROUND

This invention relates to the treatment of occluded blood vessels, and in particular to the location and display of occluded portions of vessels on 3-D angiographic images.

Three dimensional angiographic is a valuable imaging technique in which contrast agent is introduced into the subject's vasculature and a three dimensional image of the vasculature is made with an appropriate imaging system such as an x-ray or MR imaging system. Three dimensional angiography provides an accurate image of the vasculature that among other things reveals occluded portions of the vasculature, which, because of the occlusion, contain little or no contrast agent, and thus are not as visible in the resulting angiogram.

With the advent of remote navigation techniques for navigating medical devices through a subject's vasculature, angiograms are used for planning and conducting vascular navigation. However the gaps in angiograms caused by occlusions impair the use of angiograms for planning and conducting navigations. This is particularly true in the treatment of vascular occlusions because to navigate successfully through an occluded vessel, for example to remove the occlusion, it is important to know the location of the vessel.

SUMMARY

Embodiments of this invention provide methods of locating and displaying the location of occluded blood vessels which are generally difficult or impossible to see in 3D angiograms. One preferred embodiment provides a method of finding the location of an occluded portion of a blood vessel relative to a three-dimensional angiographic image of a subject's vasculature. This method generally comprises identifying the location of the occluded portion of the blood vessel on each of a series of displayed two dimensional images that are derived from the three dimensional image data in planes that are substantially transverse to the direction of the occluded portion of the vessel. These identified locations are connected together to define the path of the occluded vessel, which can be displayed on the three-dimensional angiographic image.

Embodiments of this invention make it possible to locate and display occluded portions of a subjects vasculature that are difficult or impossible to locate in conventional angiograms. With some embodiments it is possible to obtain sufficiently accurate location information to permit remote navigation through the occluded portion, and if desired, to open occluded blood vessels. These and other features and advantages will be in part apparent and in part pointed out herein after.

BRIEF DESCRIPTION OF THE DRAWINGS

FIG. 2 is an enlarged schematic view of a vasculature branch with an occlusion, showing a series of planes from which two dimensional images from the three dimensional images can be displayed to locate the occluded portion of the vessel;

FIG. 3 is a schematic view of a two-dimensional image taken along one of the planes shown in FIG. 2, illustrating a first technique identifying the location of the occluded portion of a blood vessel;

FIG. 4 is a schematic view of a two-dimensional image taken along one of the planes shown in FIG. 2, illustrating a second technique of identifying the location of the occluded portion of a blood vessel;

FIG. 5 is a schematic view of a two-dimensional image taken along one of the planes shown in FIG. 2, illustrating a fourth technique of identifying the location of the occluded portion of a blood vessel;

FIG. 6 is a schematic view of a two-dimensional image taken along one of the planes shown in FIG. 2, illustrating a fifth technique of identifying the location of the occluded portion of a blood vessel;

Correspondence reference numerals indicate corresponding parts throughout the several views of the drawings.

DETAILED DESCRIPTION

Generally embodiments of the present invention provide methods finding the location of an occluded portion of a blood vessel relative to a three-dimensional angiographic image of a subjects vasculature. Once the position of the occluded portion of the blood vessel has been determined, this information can be used to navigate through the occluded vessel, or at least to display the position of the occluded vessel.

The method of the preferred embodiment of this invention comprises identifying the location of the occluded portion of the blood vessel on each of a series of displayed two dimensional images derived from the three dimensional image data that are in planes that are substantially transverse to the direction of the occluded portion of the vessel.

Figure 1:
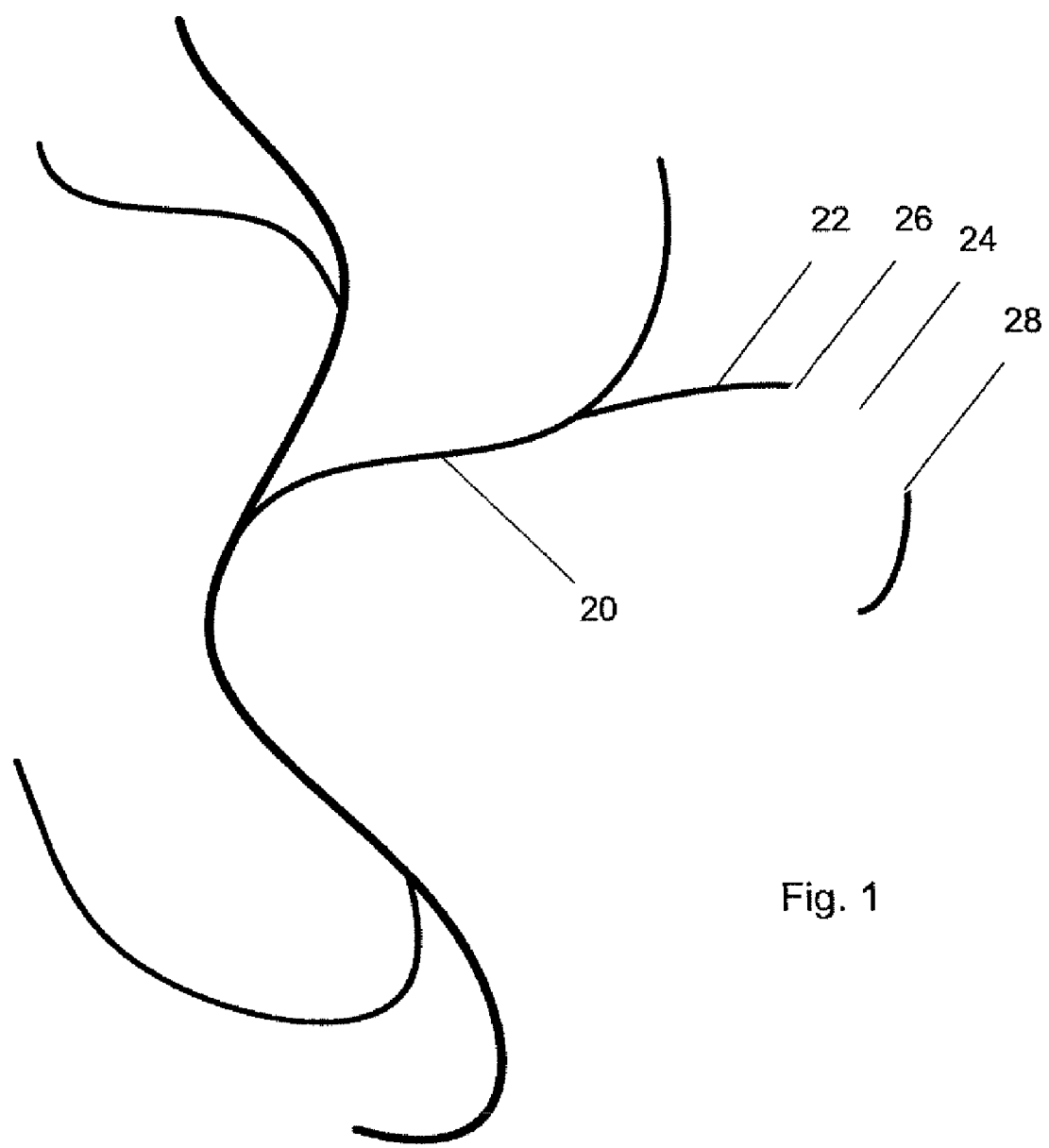
FIG. 1 is a schematic view of a three dimensional angiogram, showing an occluded portion in the vasculature.

A three-dimensional vascular tree from a three dimensional angiogram is indicated generally as 20 in FIG. 1. The vascular tree 20 can be generated from any three-dimensional imaging system, including but not limited to x-ray, CT or MR imaging. As shown in FIG. 1, the vascular tree 20 comprises a plurality of branches, and might represent, for example the coronary vasculature. One of the branches 22 has a gap 24, that is identifiable as having a start 26 and an end 28. This gap 24 is typically indicative of an occluded portion of the blood vessel which has reduced or no flow, so that the contrast agent cannot fill the portion and reveal the occluded portion in an image.

In order to navigate through the branch 22, it is desirable to know the location (i.e. the position and orientation) of the entire branch to minimize damage that the medical device might cause. Knowledge of the location of the branch is particularly desirable in the case of a procedure for removing or treating the occlusion, in order to ensure that the occlusion is being removed, but the vessel remains intact.

While occluded vessels are generally not visible or are only minimally visible, in three dimensional volume rendered angiograms, the profile of even an occluded vessel can often be resolved in a two-dimensional cross sectional view. Thus as shown schematically in FIG. 2, in accordance with the preferred embodiment of the methods of this invention, a plurality of two dimensional images in planes generally transverse to the expected path of the occluded portion 24 of the branch 22 are derived from the three dimensional imaging data. As shown schematically in FIG. 2, images are made in 5 planes 30A, 30B, 30C, 30D, and 30E, but the number of images used will depend upon the length of the occluded section, the geometry of the occluded section (i.e. whether it is substantially straight or tortuous), and the anticipated use of the location information (i.e. generally lesser resolution for simple navigations, and generally greater resolution for procedures attempting to remove the occlusion).

Each of the images from the planes is displayed, and the user can discern the location of the occluded vessel in the image and mark it in some manner. By marking the location of the vessel in each of a series of images, the path of the vessel can be determined even though it is not readily visible in the three dimensional angiogram. The path of the occluded portion can thus be displayed on the three dimensional angiogram, and the location information can be used to control navigations through the occluded portion and it can be used in a procedure removing the occlusion.

Figure 7:
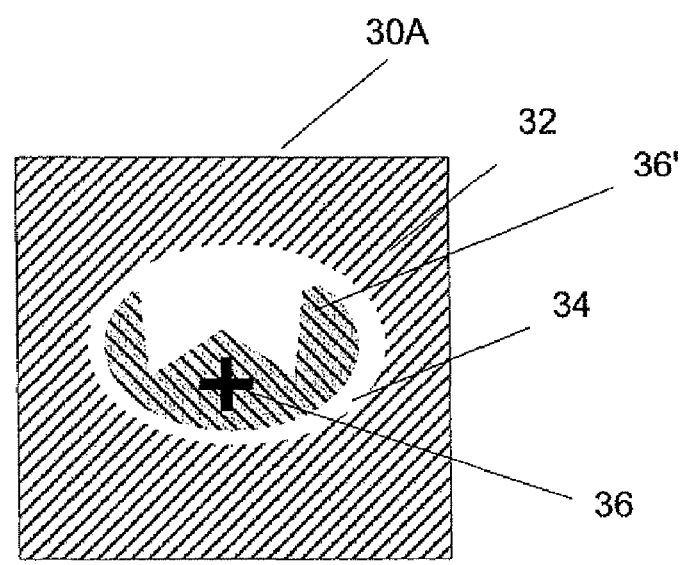
FIG. 7 is a schematic view of a two-dimensional image taken along one of the planes shown in FIG. 2, illustrating third technique method of identifying the location of the occluded portion of a blood vessel.

For example, as shown in FIG. 3, the two dimensional image from plane 30A is displayed and the user can discern the wall 34 from the background 32 of the image and even from the occlusive material 34 inside the vessel. The user can then mark what appears to be the centerline of the occluded portion of the vessel, for example by positioning a cursor 36 (which can be manipulated by a mouse or joystick or other device and clicking. Of course, as shown in FIG. 4, the user might select an off center location, if desired, for example to stay away from the inside or outside of a bend in the vessel, or in the case of a partially occluded vessel as shown in FIG. 7, to identify a path through the occluded portion of the vessel. Alternatively, instead of identifying a position in the vessel, the user might identify the vessel itself. Thus as shown in FIG. 5, the user might use a conventional oval drawing tool 40 to identify the vessel wall 34, which is typically circular to elliptical. Alternatively, as shown in FIG. 6, the user might use a conventional line drawing tool to draw two or more chords across the occluded vessel, the ends of which can be used to derive a circle or oval to approximate the vessel wall 24, which approximation is preferably displayed so that the user can adjust it if necessary. Alternatively, image processing programs can automatically detect either a point inside the occlusion or the vessel wall which can either be used directly, or simply displayed to facilitate the user selection, allowing the user to approve or to adjust and approve the automatically selected position.

Figure 8:
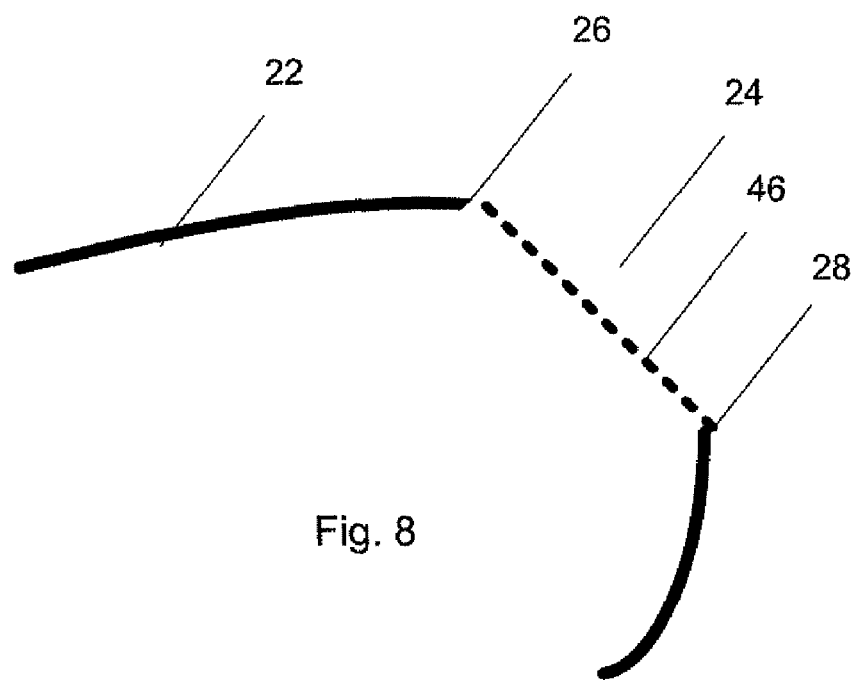
FIG. 8 is an enlarged schematic view of a vasculature branch with an occlusion, showing one technique for predicting the path of the occluded portion of the vessel.
Figure 9:
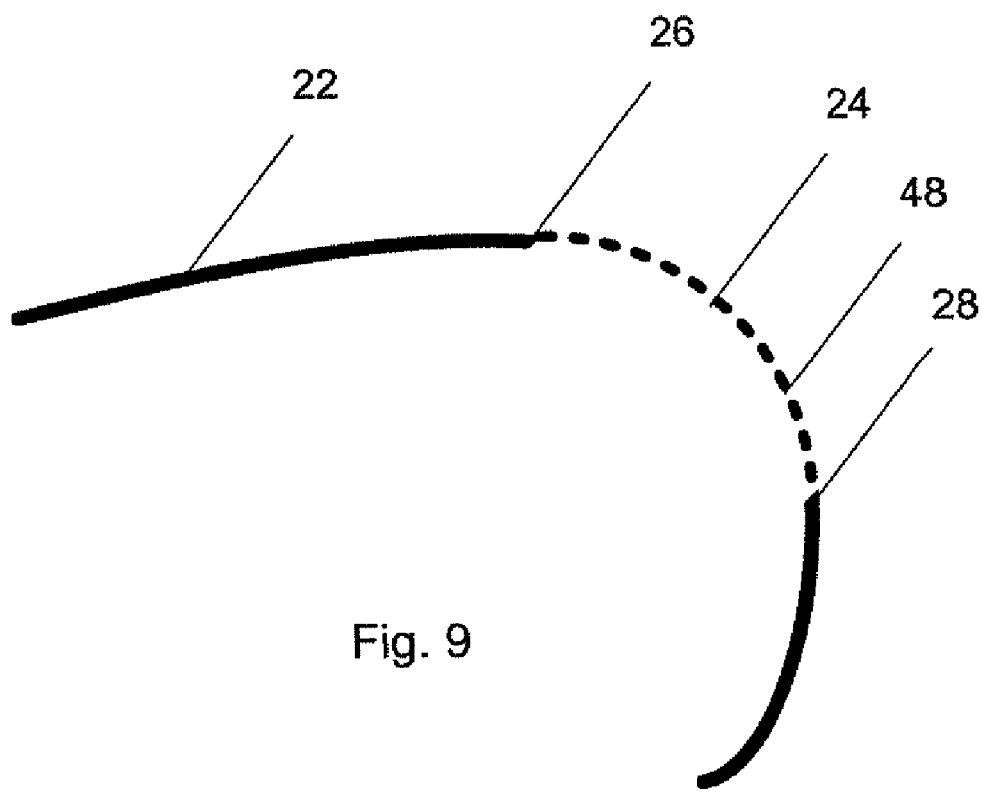
FIG. 9 is an enlarged schematic view of a vasculature branch with an occlusion, showing a second technique for predicting the path of the occluded portion of the vessel.
Figure 10:
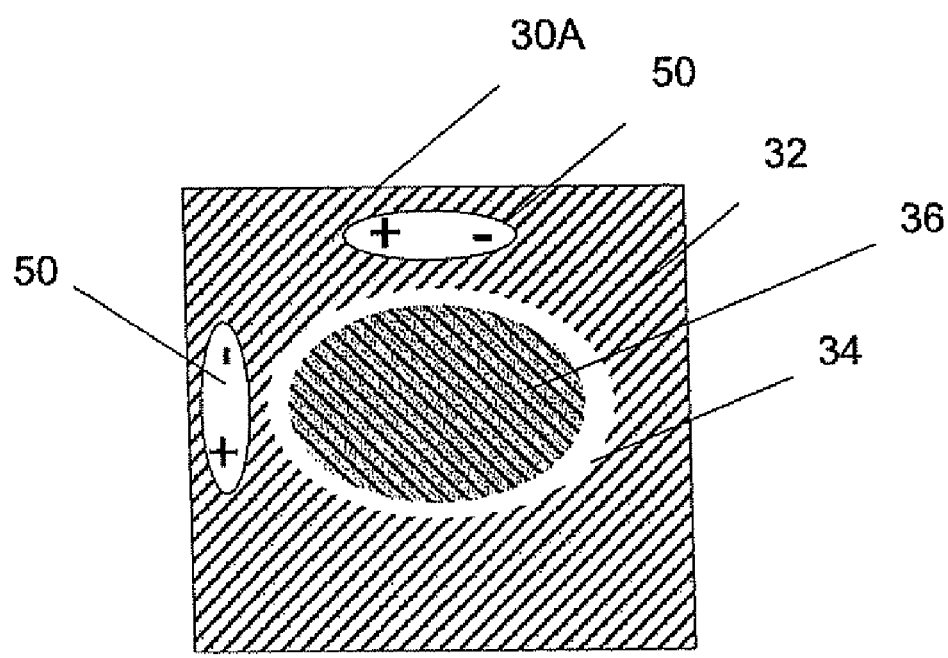
FIG. 10 is a schematic view of a two-dimensional image taken along one of the planes shown in FIG. 2, illustrating a method of adjusting the plane in which the image is taken to facilitate identifying the location of the occluded portion of a blood vessel.

The two-dimensional images are preferably generally transverse, and more preferably generally perpendicular to the direction of the occluded vessel so that the vessel cross section is easier to detect. To facilitate this, the user can identify the start 26 and end of 28 of the occluded portion, and as shown in FIG. 8, a straight line path 46 can be predicted between the start and the end of the occluded portion. The two dimensional displayed images can then be taken in planes transverse, more preferably in a plane perpendicular to the predicted path 46. As shown in FIG. 9 a more accurate prediction of the path of the occluded path can be made by using the direction of the non-occluded portion of the vessel adjacent to the start 26 of the occluded portion, and the direction of the non-occluded portion of the vessel adjacent to the end 28, and fitting a smoothly curved path 48 between the start and end points. The two dimensional displayed images can then be taken in planes transverse to the predicted path 48. Thus the path of the occluded portion of the blood vessel can be found using a series of images in parallel or non-parallel planes.

In a first alternative embodiment the displayed image is manually tiltable by the user to adjust the plane in which the image is taken. Tilt controls 50 can be provided on the image so that the user can tilt the image so that the plane of the image is as transverse as possible to the occluded vessel direction, to facilitate the identification of the location of the occluded vessel portion. As a general rule, the vessel will appear most clearly in a perpendicular cross section, although the vessel will also appear smallest in such a view. In a second alternative, rather than require the user to adjust the orientation of the plane, a plurality of images can be displayed each in a plane with a slightly different orientation, and the user can use whatever image in which the vessel appears clearest. The selection process can be automated, and through visual processing the image from the most advantageous plane can be automatically selected and displayed for the user.

The region in which the occluded portion is located is preferably identified by marking a volume on the three dimensional angiogram, or by at least marking the start and preferably the start and end points of the occlusion, to reduce the amount of data that must be processed, and to facilitate the generation of the two dimensional displays from the three dimensional data set. In an automated system, the identification and recognition of the non-occluded portions can result in the automatic identification of the gaps.

In a user interface that implements the methods of the preferred embodiments of this invention, software would preferably compute optimal x-ray viewing angles for the vessel. The "optimal" viewing angles about the x-ray vessel are typically those which rotate the c-arm about the vessel axis. These are optimal because one wants to monitor how well a guidewire or other device remains centered within the vessel lumen, and this needs to be done by rotating the c-arm and taking x-rays from more than one view. Ideally the views would be separated by 90 degrees, but constraints imposed by the navigation system, patient table, and other equipment don't always permit this. However, the software could take this into account to help the user position x-rays optimally for monitoring treatment device positioning within an occluded vessel. Once calculated, the x-ray view angles could be either transmitted directly to the x-ray system or displayed to the user so that they could move the x-ray system themselves.

In x-rays of an occluded vessel, one can normally see the vessel right up to the point of the occlusion, sometimes on either side of the occlusion. A medical device, such as a microcatheter could be pushed right up to the edge of the occlusion, and then be used as a "local reference point" so that the vessel path extracted from the three dimensional dataset can be more precisely registered to an x-ray. This forms a "floating" reference system, in that manipulations of a treatment device extended from microcatheter would always be relative to the "local reference point", and thus positions during the heartbeat and respiration could be more precisely established. In an ideal embodiment, the treatment device and catheter positions would be localized extremely precisely through a system such as Mediguide (http://www.mediguide.co.il/). The computation of the position relative to the catheter could be used to compute a relevant CT image of the vessel cross-section, allowing the user to know whether the treatment device is off center of the vessel lumen, and also to show what is ahead and behind the treatment device as it moves across an occlusion. In another embodiment, the position of the catheter and treatment device can be localized by x-ray image processing and used to compute the deviation of the treatment device from the vessel lumen. However, with the x-ray image processing technique, the user would still have to move the x-ray c-arm about the vessel axis in order to monitor the centering in three dimensions.

Operation

In operation the occluded portion of a blood vessel can be quickly and accurately identified by identifying the location of the occluded portion of the blood vessel on each of a series of displayed two dimensional images derived from the three dimensional image data in planes substantially transverse to the direction of the occluded portion of the vessel. The locations identified on each of the images can be used to determine the path of the occluded vessel, even if it not readily visible in three dimensional imaging. This location information can be used to facilitate the operation of medical navigation system and to facilitate procedures for removing the occlusion and opening the vessel. The raw data can be used, or the data can be used to derive and display a construction of the occluded vessel on the three dimensional angiogram, although the display would preferably differentiate between actual portions and constructed portions of the images.

A prediction of the path of the occluded portion is preferably made, and the displayed two dimensional images are taken from planes that are perpendicular to the displayed path. The predicted path can be derived from the locations of the start and end of the occluded portion, or a more accurate prediction can be made by taking into account the directions of the non-occluded portions of the blood vessel adjacent the occluded portion of the blood vessel. Furthermore, the predicted path of the occluded portion of the blood vessel can be updated as information about the location of the occluded portion of the blood vessel identified on the displayed two dimensional images is obtained.

Depending upon user preference and how the information about the location of the occluded portion will be used, the user can identify a point near the center of the occluded portion of the blood vessel or purposely identify another point away from bending walls of the vessel or through a partial occlusion in the vessel. Rather than identifying a point in the occluded vessel, the user could identify the vessel itself, for example drawing a loop around the vessel or drawing two or more intersecting chords to identify the vessel walls.

The displayed images can be from a series of parallel planes or they can be from planes of different orientations according to the contour of the occluded vessel. The orientation can be made adjustable, or a plurality of alternative planes can be displayed to facilitate the identification of the occluded portion of the vessel.

Of course some or all of the process can be automated, including the determination of the planes in which to take images, the processing of the imaging data in each plane to identify the occluded portion of the blood vessel, and the processing of the individual locations in the occluded vessel to determine the overall path of the occluded vessel.

What is claimed is:

1. A method of finding the location of an occluded portion of a blood vessel relative to a three-dimensional angiographic image of a subject's vasculature, the method comprising:
   deriving, from three dimensional image data associated with an angiographic image, a series of two dimensional images in planes substantially transverse to the direction of an occluded portion of a blood vessel that is displayed in the angiographic image;
   identifying, via a user-input device, a location within the occluded portion of the blood vessel on each of the series of displayed two dimensional images derived from the three dimensional image data; and
   determining, from the locations identified on each of the two dimensional images, a construction of the occluded portions of the blood vessel, and displaying the construction on the three-dimensional angiographic image to indicate the location of the occluded portions.

2. The method according to claim 1 further comprising predicting the path of occluded portion, and wherein the displayed two dimensional images are from planes perpendicular to the displayed path.

3. The method according to claim 1 wherein predicting the path of the occluded portion takes into account the locations of the start and end of the occluded portion.

4. The method according to claim 3 wherein predicting the path of the occluded portion takes into account the direction of the non-occluded portions of the blood vessel adjacent the occluded portion of the blood vessel.

5. The method according to claim 2 wherein the predicted path of the occluded portion of the blood vessel is updated at least once using information about the location of the occluded portion of the blood vessel identified on the displayed two dimensional images.

6. The method according to claim 1 wherein the step of identifying the location of the occluded portion of the blood vessel comprises identifying a point near the center of the occluded portion of the blood vessel.

7. The method according to claim 1 wherein the step of identifying the location of the occluded portion of the blood vessel comprises identifying the cross-section of the occluded portion of the blood vessel.

8. The method according to claim 7 wherein the step of identifying the cross section of the occluded portion of the blood vessel comprises making a closed loop around the periphery of the occluded portion of the blood vessel.

9. The method according to claim 7 wherein the step of identifying the cross section of the occluded portion of the blood vessel comprises marking two intersecting chords across the cross section.

10. A method of locating an occluded portion of a blood vessel relative to a three-dimensional angiographic image of a subject's vasculature, the method comprising:
    successively displaying two dimensional images, derived from the three dimensional image data, of a plane substantially transverse to the expected local direction of the vessel that includes the occluded portion of the vessel;
    identifying, via a user-input device, a location within the occluded portion of the vessel on each of the displayed two dimensional images; and
    displaying a construction determined from the locations identified on each of the two dimensional images on the three-dimensional image to indicate the location of the occluded portions.

11. The method according to claim 10 further comprising identifying the starting point of the occluded portion of the blood vessel.

12. The method according to claim 11 further comprising determining a predicted path of the occluded portion of the blood vessel based upon the direction of the non-occluded portion adjacent the starting point of the occluded portion, and wherein the orientation of the plane of at least the first two dimensional image is perpendicular to the predicted path.

13. The method according to claim 12 further comprising determining a predicted path of the occluded portion or the blood vessel based upon the direction of the non-occluded portion adjacent the starting point of the occluded portion, and wherein the orientation of the plane of the first two dimensional image is perpendicular to the predicted direction, and wherein the orientation of the successive planes is perpendicular to the predicted path of the occluded portion based at least in part upon a location of the occluded portion identified on one of the previous displayed two dimensional image.

14. The method according to claim 10 wherein the step of identifying the location of the occluded portion of the blood vessel comprises identifying a point near the center of the occluded portion of the blood vessel.

15. The method according to claim 10 wherein the step of identifying the location of the occluded portion of the blood vessel comprises identifying the cross-section of the occluded portion of the blood vessel.

16. The method according to claim 15 wherein the step of identifying the cross section of the occluded portion of the blood vessel comprises making a closed loop around the periphery of the occluded portion of the blood vessel.

17. The method according to claim 15 wherein the step of identifying the cross section of the occluded portion of the blood vessel comprises marking two intersecting chords across the cross section.

18. The method according to claim 10 further comprising identifying the starting and ending points of the occluded portion of the blood vessel, and wherein the planes are perpendicular to a straight line connecting the starting and ending points.

19. The method according to claim 10 further comprising identifying the starting and ending points of the occluded portion of the blood vessel, and wherein the planes are perpendicular to a curve connecting the starting and ending points derived in part from the direction of the non-occluded portions of the blood vessel adjacent the occluded portion.

20. The method according to claim 10 further comprising adjusting the orientation of the plane of the displayed two dimensional image before at least some identification steps.

21. The method according to claim 10 further comprising displaying a plurality of two dimensional images at different angular orientations, and wherein the step of identifying the location of the occluded portion of the lumen comprises identifying the occluded portion of the lumen on one of the displayed images.

22. A method of locating an occluded portion of a blood vessel in a three-dimensional angiographic image of a subject's vasculature, the method comprising:
    predicting the path of the occluded portion of the blood vessel;
    displaying a plurality of two dimensional images, derived from the three dimensional image data, of a plane substantially transverse to the predicted path of the occluded portion of the vessel, where the displayed two dimensional images include the occluded portion of the vessel;
    identifying, via a user-input device, a location within the occluded portion of the vessel on each of the displayed two dimensional image; and
    displaying a construction determined from the locations identified on each of the two dimensional images on the three-dimensional image to indicate the location of the occluded portions.

23. The method according to claim 22 further comprising updating the predicted path of the occluded portion of the blood vessel based in part on at least one of the locations of the occluded portion identified on a displayed two-dimensional image.

24. A method of identifying a navigation path through an occluded portion of a blood vessel that is difficult to see on a three-dimensional angiographic image, the method comprising:
    identifying, via a user-input device, a location within the occluded portion of the blood vessel on each of a series of displayed two dimensional images, derived from the three dimensional image data, in planes substantially transverse to the direction of the occluded portion of the blood vessel; and
    determining the navigation path through the occluded portion of the blood vessel by connecting the identified locations.

25. The method according to claim 24 further comprising positioning imaging equipment to image in a direction substantially perpendicular to the navigation path.

* * * * *